United States Patent [19]

Sunshine et al.

[11] Patent Number: 5,100,918

[45] Date of Patent: Mar. 31, 1992

[54] PREVENTION OR TREATMENT OF SUNBURN USING THE S(+) ISOMER OF IBUPROFEN

[75] Inventors: Abraham Sunshine, New York; Eugene M. Laska, Larchmont, both of N.Y.

[73] Assignee: Sterling Drug, Inc., New York, N.Y.

[21] Appl. No.: 593,784

[22] Filed: Oct. 5, 1990

Related U.S. Application Data

[63] Continuation-in-part of Ser. No. 356,850, May 25, 1989, Pat. No. 4,980,375, which is a continuation-in-part of Ser. No. 71,914, Jul. 10, 1987, Pat. No. 4,851,444.

[51] Int. Cl.$^5$ ............................................. A61K 31/19
[52] U.S. Cl. .................................................. 514/557
[58] Field of Search ............................... 514/570, 557

[56] References Cited

PUBLICATIONS

S. S. Adams et al., 1975, *Curr. Med. Res. Opin.* 3(8):552, "The Optical Isomers of Ibuprofen".
S. S. Adams et al., 1976, *J. Pharm. Pharmacol.*, 28:256–257, "Pharmacological Differences Between the Optical Isomers of Ibuprofen: Evidence for Metabolic Inversion of the (−)-Isomer".
T. Y. Shen, 1972, In *Angewandte Chem. Internat. Ed.* 11(6):460–472, "Perspectives in Nonsteroidal Anti-Inflammatory Agents".
Edwards et al., *Arch. Dermatol. Res.*, 272:263–267, "Reduction of Erythema Response to UV Light by Nonsteroidal Anti-Inflammatory Agents".
A. J. Hutt et al., 1983, *J. Pharm. Pharmacol.* 35:693–704, "The Metabolic Chiral Inversion of 2-Arylpropionic Acids-A Novel Route with Pharmacological Consequences".
Lim et al., 1983, *J. Invest. Dermatol.* 81(5):455–458, "Effects of Indomethacin on Alterations of ATPase-Positive Langerhans Cell Density and Cutaneous Sunburn Reaction Induced by UV-B Radiation".
Snyder et al., 1974, *J. Invest. Dermatol.* 62(1):47–50, "Intradermal Anti-Prostaglandin Agents and Sunburn".
Snyder et al., 1974, *Br. J. Dermatol.* 99–91, "Topical Indomethacin and Sunburn".

*Primary Examiner*—S. J. Friedman
*Attorney, Agent, or Firm*—Burns, Doane, Swecker & Mathis

[57] ABSTRACT

Ultraviolet radiation induced erythema is prevented or treated in a human mammal in need of such prevention or treatment, i.e., a mammal suffering from or seeking to avoid sunburn, by topically administering thereto a unit dosage erythema-preventing or treating effective amount of the S(+) ibuprofen enantiomer, said enantiomer being substantially free of its R(−) ibuprofen antipode.

54 Claims, No Drawings

PREVENTION OR TREATMENT OF SUNBURN USING THE S(+) ISOMER OF IBUPROFEN

CROSS-REFERENCE TO RELATED APPLICATIONS

This is a continuation-in-part of our pending application Ser. No. 356,850 filed May 25, 1989, now U.S. Pat. No. 4,980,375 which is a continuation-in-part of our application, Ser. No. 071,914, filed July 10, 1987, now U.S. Pat. No. 4,851,444, both of which are hereby expressly incorporated by reference and relied upon.

BACKGROUND OF THE INVENTION

1. Field of the Invention

The present invention relates to the use of topically administered S(+) ibuprofen to prevent or treat erythema induced by ultraviolet irradiation in mammalian organisms in need of such prevention or treatment, and to certain topical pharmaceutical compositions comprising unit dosage effective amounts of S(+) ibuprofen.

2. Description of the Prior Art

Ibuprofen, or (+) 2-p-isobutylphenyl)propionic acid, has the structural formula

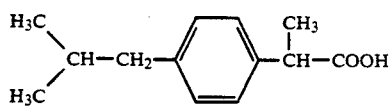

The compound is well-known as a nonsteroidal anti-inflammatory drug having analgesic and antipyretic activity. Ibuprofen is currently marketed by prescription in the United States generically, as well as under tradenames such as Motrin ®, which is available in 400, 600 and 800 mg tablets for oral administration. Ibuprofen has recently also become available in this country in non-prescription strength (200 mg) under a variety of tradenames, including Advil ® and Nuprin ®, as well as in generic form. For the treatment of mild to moderate pain, 400 mg every 4 to 6 hours, not to exceed 3200 mg daily, is generally recommended for Motrin ®. The lower dose over-the-counter products are generally recommended for minor aches and pains, to be used orally at the 200 to 400 mg level, every 4 to 6 hours, not to exceed 1200 mg daily unless directed by a physician. See also *Physician's Desk Reference*, 40th edition, 1990, publisher Edward R. Barnhart, Medical Economics Company, Inc., Oradell, NJ 07649.

As is apparent from its chemical nomenclature, ibuprofen is a racemic mixture. It is only the racemic mixture which has in fact ever been marketed. There have, however, been some studies of the individual S(+) and R(−) isomers reported in the literature. These generally reflect that the R(−) isomer is converted in vivo but not in vitro to the S(+) enantiomer, which is the active form of ibuprofen.

Adams et al, *Curr. Med. Res. Opin.*, 3, 552 (1975) and *J. Pharm. Pharmacol.* 28, 256–257 (1976), reported that in vivo anti-inflammatory and analgesic tests in guinea pigs, rats and mice comparing the dextro (+), levo (−) and racemic mixture forms of ibuprofen showed the three forms to be very similar in potency. (The in vivo tests were conducted in an acetylcholine-induced writhing test in the mouse, in a pain threshold technique test using the yeast-inflamed paw of the rat and using ultraviolet erythema in the guinea pig.) In vitro. however, it was found that nearly all of the activity resided in the dextrorotatory form. The authors concluded that the in vitro results suggested that only the dextro (+) form was the active one, but that in vivo the levo form was converted to the dextro form so that there was little difference in pharmacological activity. This was also seen to be an explanation for earlier observations [Adams et al, *J. Pharm. Sci.*, 56, 1686 (1967) and Mills et al, *Xenobiotica*, 3, 589–598 (1973)] that ibuprofen's urinary metabolites in man were found to be dextrorotatory. Thus, it has been recognized for over a decade that the S(+) isomer is the active form.

Wechter et al, *Biochem. Biophys. Res. Commun.*, 61, 833–837 (1974) reported the results of tests in healthy human subjects designed to determine the stereochemistry involved in ibuprofen's metabolism and the relative stereochemical relationships between ibuprofen's optical isomers and its metabolic products. They found there was a facile epimerization of ibuprofen's R(−) isomer to the S(+) isomer and concluded that this accounted for the essential bioequivalence of the R(−) and S(+) isomers.

Related observations were reported by Vangiessen et al, *J. Pharm. Sci.*, Vol 64, No. 5, 798–801 (May 1975), who found that after oral administration of the racemic mixture to human volunteers, the predominant enantiomer in the peripheral circulation and excreted in the urine was of the d-configuration. Vangiessen et al estimated that the plasma drug disappearance half-lives for the d- and l-isomer were 3.34 and 2.01 hours, respectively. The concentration ratio of d to l increased progressively with time from 1.17 at one hour to 2.65 at eight hours; however, these estimates are compromised by the small sample size (n=3), the fact that normal subjects were used, and the extremely large standard deviations from the mean at the earliest (one-hour) post-dosing time point. Interpretation of the results of this study is further compromised because S(+) was not administered alone so that no comparisons with the racemate are possible.

Subsequently, Kaiser et al., *J. Pharm. Sci.*, Vol. 65, No. 2, 269–273 (February 1976) reported on characterization of enantiomeric compositions of ibuprofen's major urinary metabolites after oral administration of the racemic mixture and the individual S(+) and R(−) isomers to healthy human subjects. It was found that only the R(−) enantiomer of the intact drug was inverted to its optical antipode, S(+).

Hutt et al, *J. Pharm. Pharmacol.*, 35, 693–704 (1983), reviewed the earlier work on the metabolic chiral inversion of 2-arylpropionic acids, including ibuprofen, which they indicate was the first substituted 2-arylpropionic acid conclusively shown to undergo the inversion as well as the most studied member of the group. The authors again noted that Adams et al (1976) found no significant difference in in vivo activity among the R(−) and S(+) isomers and the racemic mixture in three different animal models, but very large differences in vitro between the R(−) and S(+) isomers, ascribing this discrepancy to the virtually quantitative conversion of the R(−) to the active S(+) isomer in vivo. Hutt et al indicated similar properties for fenoprofen. The enantiomers of fenoprofen were reported to be of equal potency in animal test systems.

In the same paper, Hutt et al reported that, in contrast, for several other 2-arylpropionic acids, the inactive R(−) isomer was not converted in vivo to the active S(+) isomer as readily as ibuprofen and fenoprofen, although the conversion seemed to occur to some extent over time. Naproxen, they noted, has been the only compound marketed as the S(+) enantiomer to date. And in the case of indoprofen, the R(−) enantiomer was found to be about 20 times less pharmacologically active in rats and mice in vivo than the S(+) isomer. Hutt et al concluded:

> It is likely that benefits will be obtained from the use of the S(+)-enantiomer of 2-arylpropionates as drugs as opposed to the racemates. This is only found at present in the case of naproxen. In cases of rapid inversion, the inactive R(−) isomer serves merely as a prodrug for the active S(+)-antipode. Where inversion is slow, the R(−) enantiomer is an unnecessary impurity in the active S(+) form. Use of the S(+)-enantiomer would permit reduction of the dose given, remove variability in rate and extent of inversion as a source of variability in therapeutic response and would reduce any toxicity arising from non-stereospecific mechanisms.

Thus, in cases of rapid inversion, such as ibuprofen and fenoprofen, where substantially equivalent in vivo responses have been reported for the individual enantiomers and the racemic drug, Hutt et al suggested that no benefits would be obtained from the use of the S(+) isomer because the inactive R(−) isomer merely acts as a prodrug for the active S(+) form. Contrariwise, in cases where chiral inversion is slow, e.g., naproxen and indoprofen, the use of the S(+) enantiomer is desirable for several reasons enumerated by Hutt et al. Indeed, naproxen has been reported to be marketed as the d-isomer for one of the reasons given by Hutt et al, i.e., to reduce side effects (Allison et al, "Naproxen," Chapter 9 in *Anti-inflammatory and Anti-Rheumatic Drugs*, eds. Rainsford and Path, CRC Press Inc., Boca Raton, FL., 1985, p. 172).

Another general report on earlier work has been provided by Hutt et al in *Clinical Pharmacokinetics*, 9, 371-373 (1984). In this article on the importance of stereochemical considerations in the clinical pharmacokinetics of 2-arylpropionic acids, the authors tabulated relative potencies of the enantiomers of a number of 2-arylpropionic acids in vivo and in vitro. The in vitro results showed the S or (+) isomer in each case to be the active species. In vivo, however, the results were not consistent across the entire class. Thus, the results for naproxen and indoprofen demonstrate the S or (+) isomer to be much more active in vivo, indicating a relatively slow inversion of the inactive R or (−) isomer to the active S or (+) isomer; the results for fenoprofen and ibuprofen, on the other hand, demonstrate the inactive R or (−) and the active S or (+) isomers to be approximately equally effective in vivo. indicating a rapid inversion of R or (−) isomer to S or (+) isomer.

The medicinal chemistry of 2-arylpropionic acids and other NSAIDs (non-steroidal anti-inflammatory drugs) has been reviewed by Shen in *Angewandte Chemie International Edition*, Vol. 11, No. 6, 460-472 (1972) and in "Nonsteroidal Anti-Inflammatory Agents," Chapter 62 in Burger's Medicinal Chemistry, 4th edition, Part III, Wiley Interscience, New York (1981), pp. 1205-1271. In the former publication, Shen notes that ibuprofen is used as a racemic mixture because the two optical isomers are equally potent in the UV erythema assay, a commonly used anti-inflammatory model.

Lee et al, *Br. J. Clin. Pharmac.* 19, 669-674 (1985), administered racemic ibuprofen and each of the enantiomers separately to four healthy human males, then studied stereoselective disposition. They estimated that about 63% of the dose of R(−) was inverted to the S(+) enantiomer over a 14 hour period. Lee et al noted that the kinetics of the S(+) and R(−) enantiomers were changed when the respective optical antipode was concurrently administered. The authors speculated that this alteration reflected an interaction between the R(−) and S(+) forms at the binding sites for plasma protein. An ibuprofen plasma level time profile for a single subject is shown graphically in the paper and might suggest that there was minimal conversion in the early hours of the study, but the authors did not appear to attach any significance to this. Lee et al indicated that the half-life of S(+) after administering the racemate was 2.5 hours, whereas the half-life of S(+) after administering S(+) was 1.7 hours. The authors recognized the limitations of their work, for reasons including the small number of subjects studied, and an assumption that the clearance of S(+) is unchanged between administrations of R(−) and S(+). They also cautioned that it is quite likely that the fraction of R(−) that is inverted to S(+) varies from individual to individual.

Cox et al, *J. Pharmacol. Exp. Ther.*, Vol. 232, No. 3, 636-643 (1985), carried out liver perfusion experiments to study the role of the liver in the clearance of the stereoisomers of ibuprofen in normal and disease states. Experiments were conducted with normal and fatty rat liver. Results showed that when liver is fatty, clearance of the R(−) isomer is affected and preferential S(+) hepatic distribution is eliminated. However, the effects were predicted to have only minimal impact on total ibuprofen plasma levels following racemic ibuprofen dosing.

Cox et al, abstract in *Amer. Soc. Clin. Pharmacol. Ther.*, February 1987, 200 (abstract PIIL-7) described a three way crossover study in which single doses of ibuprofen solution were given orally to twelve healthy human males. The doses given were 800 mg of racemic ibuprofen, 400 mg of R(−) ibuprofen and 400 mg of S(+) ibuprofen. Based on area-under-the-curve measures, significant chiral inversion was observed for R(−) but not for S(+). Elimination of S(+) was inhibited as plasma concentration of R:S increased. The extent of R(−) inversion, based on urinary data, was the same for the racemate and the R(−) isomer, with a mean of .66. Again, the authors gave no information as to what occurred in the first two hours. The statement on reduced clearance of S(+) in the racemate is consistent with the finding of increased length of S(+) half-life after administering the racemate found by Lee at al.

Laska et al, *Clin. Pharmacol. Ther.*, Vol. 40, No. 1, 1-7 (July 1986), reported that administration of racemic ibuprofen to patients with moderate to severe pain subsequent to third molar extraction gave correlations between pain intensity ratings and serum levels of ibuprofen. Correlations were found between contemporaneous serum levels and measures of pain intensity improvement, supporting the proposition that increased ibuprofen serum levels lead to increased analgesia, particularly in the first few hours after dosing. However, the authors did not correlate analgesia with either isomer of ibuprofen; the possibility of critical differences between free and bound ibuprofen and between the S(+) and R(−) isomers was not addressed.

A considerable amount of effort has been spent in the search for a method to prevent the occurrence of, or alternatively, to treat sunburn. Sunburn is caused by certain wavelengths of ultraviolet (UV) radiation striking the skin. The ultraviolet light alters the keratinocytes in the basal layer of the epidermis. A slight alteration results in erythema, and a severe alteration causes bullae to form from the fluid collected in the epidermis. To produce a suntan, ultraviolet light stimulates the melanocytes in the germinating layer to generate more melanin and oxidizes melanin already in the epidermis. Both of these processes serve as protective mechanisms by diffusing and absorbing additional UV radiation. The effects of the sun on the skin usually begin to appear anywhere from 1 to 24 hours after exposure and range from mild erythema to tenderness, pain, and edema. Severe reactions due to excessive exposure involve the development of vesicles or bullae as well as the constitutional symptoms of fever, chills, weakness, and shock.

Energy emissions from the sun include radiation wavelengths ranging from 200 nm to more than 18,000 nm. Ultraviolet radiation is in the 200–400 nm range, and this spectrum is subdivided into three bands.

UV-A (320–400 nm) radiation can cause tanning of the skin, but is weak in causing mild sunburn of the skin. Erythemic activity (producing redness) is relatively weak at this wavelength. The primary action of UV-A is the development of a slow natural tan. At this UV level, radiation produces some immediate pigment darkening. In addition, UV-A represents the range in which most photosensitizing chemicals are active. It is also believed that UV-A may augment the effects of UV-B.

UV-B (290–320 nm) radiation causes sunburn reaction, which also stimulates pigmentation (tanning) of the skin. It is the most effective UV radiation wavelength for producing erythema, which is why it is called sunburn radiation. It triggers new pigment formation as well as vitamin D production. In addition, it is thought to be responsible for inducing skin cancer.

UV-C (200–290 nm) radiation from sunlight does not reach the earth's surface, but artificial UV sources can emit this radiation. It does not tan the skin, but it can burn it. UV-C radiation from the sun does not reach the surface of the earth. However, UV-C is emitted by artificial ultraviolet sources. Although it will not stimulate tanning, it causes some erythema.

Other wavelengths of light also are absorbed and, if intense enough, produce erythema and burning. This type of burning differs from sunburn in that it is due to generated heat rather than a photochemical reaction.

Thus, it has been well documented that excessive exposure to ultraviolet light will cause erythema, edema, blister formation and sloughing of the skin due to cellular damage. Ultraviolet light injury includes epidermal cell death, increase in mitotic index, hyperplasia, as well as the vascular responses of vasodilation, altered permeability and cellular exudation.

The vascular changes that occur secondary to exposure to ultraviolet light are biphasic. The immediate erythema reaction is a faint, transient reddening of the skin beginning shortly after exposure to ultraviolet light and fading within 30 minutes after the exposure ends. A delayed erythema reaction appears after 2–6 hours and peaks 10–24 hours after ultraviolet-light exposure. This erythema gradually subsides over the next 2–4 days. Peeling follows 4–7 days after a moderate to severe sunburn. The mechanisms by which these two types of erythema are produced are not understood completely.

Kinins, histamine, prostaglandins, other vasoactive substances, hydrolytic enzymes, and free radicals have been implicated as mediators of the erythema caused by sunlight.

Prostaglandins have been shown to increase in erythematous skin exposed to ultraviolet B radiation. Aspirin and indomethacin which are nonsteroidal anti-inflammatory agents have been shown to inhibit the prostaglandin synthetase system in skin.

Snyder et al, "Intradermal Anti-Prostaglandin Agents and Sunburn," *The Journal of Investigative Dermatology*, Vol. 62, No. 1, 47–50 (1974) discussed the intradermal administration of indomethacin as well as aspirin to guinea pigs. The administration of each of those drugs was shown to decrease the intensity and delay the development of ultraviolet radiation induced erythema. Snyder et al, "Topical Indomethacin and Sunburn," *British Journal of Dermatology*, pp. 90–91 (1974), further demonstrated that the topical application of indomethacin in humans produced a reduction in redness, skin temperature and pain perception. It was suggested that indomethacin may be affecting sunburn by preventing biosynthesis of prostaglandins.

Likewise, several nonsteroidal anti-inflammatory drugs have been administered orally to human subjects and have been demonstrated to be effective in reducing erythema after exposure to ultraviolet radiation. In particular, Edwards et al, "Reduction of the Erythema Response to Ultraviolet Light by Nonsteroidal Anti-inflammatory Agents," *Arch. Dermatol. Res.*, Vol. 272, pp. 263–267, studied the effect of orally administered aspirin, indomethacin and ibuprofen on ultraviolet B induced erythema in human subjects. All three drugs were comparable in reducing the sunburn response to ultraviolet radiation.

Gomez et al, "Effect of Topical Diflumidone on Ultraviolet-Light-Induced Erythema," *Dermatologica*, Vol. 162, pp. 175–182 (1981) studied the topical efficacy of indomethacin and diflumidone for the suppression of ultraviolet-light-induced erythema in humans. Both indomethacin and diflumidone were found to inhibit the development of erythema; however, the indomethacin treated sites had significantly less erythema 24 hours after application.

Greenberg et al, "Orally Given Indomethacin and Blood Flow Response to UVL," *Arch. Dermatol.*, Vol. 111, pp. 328–330 (March 1975), demonstrated that orally administered indomethacin reduced the increase in blood flow produced by ultraviolet light irradiation by one-third.

Lim et al, "Effect of Indomethacin on Alteration of ATPase-Positive Langerhans Cell Density and Cutaneous Sunburn Reaction Induced by Ultraviolet-B Radiation," *Journal of Investigative Dermatology*, Vol. 81, No. 5, pp. 455–458 (1983), showed that indomethacin topically applied prior to ultraviolet-B irradiation in humans resulted in protection from the sun. Topical application of indomethacin after ultraviolet-B irradiation resulted in a decrease in erythema. The protective effect of topical indomethacin applied prior to radiation may be explained by its in vitro absorption of ultraviolet-B irradiation. The application of indomethacin after irradiation resulting in decreased erythema was probably related to its effect on prostaglandin synthetase inhibition. The authors concluded that indomethacin applied topically could be useful as a sunscreen agent. Its clinical safety and efficacy, however, remain to be determined.

Flowers et al, "A Comparative Study of the Effect of Flurbiprofen and Indomethacin on Sunburn," *Current Therapeutic Research*, Vol. 36, No. 4, pp. 787–791 (October 1984), evaluated the efficacy of ultraviolet-B induced erythema in humans when the subjects were treated with a test solution containing 2.5% indomethacin, 2.5% flurbiprofen or vehicle alone. The authors concluded that flurbiprofen showed more promise than indomethacin in the suppression of early ultraviolet-B irradiation induced erythema.

Tas et al, "Effect of Topically Applied Flurbiprofen on Ultraviolet-Induced Erythema," *Drug Intelligence and Clinical Pharmacy*, Vol. 20, 496–499 (1986), studied the effect of flurbiprofen on ultraviolet-B induced erythema in humans. The authors concluded that topical flurbiprofen decreased the dermal symptoms of sunburn. The optimum maximum concentration of flurbiprofen appeared to be approximately 3% and more than two applications appeared to have no added advantage.

In summary, the current state of the art recognizes that, in mammals, the S(+) form is the active enantiomer of ibuprofen. The art further recognizes that there is a significant, relatively rapid conversion in vivo of R(−) to S(+), with little, if any, conversion of S(+) to R(−). Furthermore, in the only animal experiments on efficacy reported in the literature, it was noted that there were no significant differences in potency between the racemate and the enantiomers in vivo. This is attributed to the rapidity of the chiral inversion. This would suggest there would be no benefit to be derived from the use of S(+) ibuprofen for any purpose. Indeed, use of S(+) alone would appear to reduce the half-life of the active drug. The prior art, moreover, is conspicuously silent in respect to any prevention or alleviation of sunburn utilizing any particular optical isomer of the ibuprofen drug species. The prior art is silent on conversion of the R(−) isomer to the S(+) isomer by the skin.

SUMMARY OF THE INVENTION

Surprisingly, the present inventors now find that S(+) ibuprofen can be advantageously topically administered to mammals, especially humans, to prevent or treat ultraviolet radiation-induced erythema and to evoke such prevention or treatment more effectively than possible by administration of the same dose of ibuprofen in its racemic form. S(+) ibuprofen is more potent than an equal amount of the racemic mixture.

This is particularly surprising in light of the art's failures to attribute any difference in activity for S(+) ibuprofen versus the racemic mixture.

In one aspect, the present invention thus provides a method for preventing ultraviolet radiation-induced erythema in a mammal, said method comprising topically administering to a mammal exposed to ultraviolet radiation an amount effective to prevent ultraviolet radiation induced erythema of S(+) ibuprofen substantially free of R(−) ibuprofen.

In another aspect, the present invention provides a method for treating ultraviolet radiation-induced erythema in a mammal, said method comprising topically administering to a mammal in need of such treatment an amount effective to treat ultraviolet radiation-induced erythema of S(+) ibuprofen substantially free of R(−) ibuprofen.

In yet another aspect, the present invention provides a pharmaceutical composition of matter for use in preventing or treating ultraviolet radiation-induced erythema in mammals, especially humans, said composition comprising an amount effective to prevent or treat ultraviolet radiation-induced erythema of S(+) ibuprofen substantially free of R(−) ibuprofen. Typically, S(+) ibuprofen is associated with a nontoxic topical pharmaceutically acceptable inert carrier or diluent therefor.

DETAILED DESCRIPTION OF THE PREFERRED EMBODIMENTS OF THE INVENTION

The term "ibuprofen" or "racemic ibuprofen" as used herein is intended to encompass not only (±) 2-(p-isobutylphenyl)propionic acid itself but also any pharmaceutically acceptable salt thereo.

The term "S(+) ibuprofen" as used herein is intended to encompass not only the dextrorotatory or S(+) isomer of 2-(p-isobutylphenyl)propionic acid, but also any pharmaceutically acceptable, antierythematously effective salt thereof. The expression "substantially free of R(−) ibuprofen" as used in conjunction with the term "S(+) ibuprofen" means that the S(+) ibuprofen is sufficiently free of R(−) ibuprofen [which is the levorotatory form or R(−) isomer of 2-(p-isobutylphenyl)propionic acid or salt thereof] to exert the desired anti-erythema effect. Practically speaking, this means that the active ingredient should contain at least 90% by weight S(+) ibuprofen and 10% or less by weight R(−) ibuprofen. Preferably, the weight ratio of S(+) ibuprofen to R(−) ibuprofen is greater than 20:1, more preferably greater than 97:3. Most preferably, the S(+) ibuprofen is 99 or more % by weight free of R(−) ibuprofen, i.e., the weight ratio of S to R is approximately equal to or greater than 99:1.

Where specific amounts of S(+) ibuprofen are set forth below, it should be understood that, unless otherwise specified, the amounts are given in mg of the acid, not of a salt. Moreover, unless otherwise specified, for simplicity's sake the amounts given represent total ibuprofen content, most of which is in the S(+) form. For example, "3 wt. % ibuprofen" means 3 wt. % of total ibuprofen at least 90% of which is in the S(+) form, preferably at least 95%, more preferably at least 97% and most preferably 99% or more.

Topical S(+) ibuprofen, in accord with the present invention, produces the following unexpected results:

(1) the S(+) isomer of ibuprofen is more potent than racemic ibuprofen for topical administration on a mammal since the ibuprofen is substantially, or in large part, in the active form; and (2) in the case of ibuprofen, the R(−) isomer is not active and would not substantially overcome the effects of ultraviolet-induced erythema or sunburn because there would probably be little if any chiral conversion in the skin.

These unexpected results can be achieved in the treatment of sunburn responsive to an NSAID (non-steroidal anti-inflammatory drug).

In a group responsive to a given dose of the racemate, it is believed that S(+) ibuprofen applied in the same amount as racemic ibuprofen would provide a better response for preventing or treating ultraviolet radiation-induced erythem. S(+) ibuprofen would be at least twice as potent.

The precise amount of topical S(+) ibuprofen for use in accord with the present invention will vary depending, for example, on the size and kind of the mammal and the condition for which the drug is administered. For use in humans, the amount effective to prevent or treat ultraviolet radiation-induced erythema of S(+)

ibuprofen will typically be from about 0.5 wt. % to about 10 wt. % although greater amounts (e.g., 15 wt. %) may be employed if needed or if tolerated by the patient. The preferred composition contains about 1 wt. % to about 5 wt. %, more preferably about 2.5 to 3.5 wt. % ibuprofen. The most preferred composition would likely contain about 3.0 wt. % ibuprofen. It should be noted, however, that lesser amounts may be useful on patients with particularly sensitive skin and/or on the skin of children.

The S(+) ibuprofen of the present invention may be applied in any vehicle or in any fashion suitable for topical administration. Topical preparations typically include solutions, e.g., clear or milky lotions, gels, creams, ointments, sprays, lip balm, clothwipe, impregnated bandages and other topical and transdermal delivery devices.

According to the FDA advisory review panel, "[a]n ideal sunscreen vehicle would be stable, neutral, nongreasy, nondegreasing, nonirritating, nondehydrating, nondrying, odorless, and efficient on all kinds of human skin. It should also hold at least 50% water, be easily compounded of known chemicals, and have infinite stability during storage". *Federal Register*, 43, 38218 (1978).

S(+) ibuprofen may be formulated with any suitable nontoxic topical pharmaceutically acceptable inert carrier material. Such topical carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, PA. 18042.

Suitable solvents or vehicles, for instance, for the topical S(+) ibuprofen composition of the present invention includes methanol, ethanol, propyl alcohol, acetone, n-butyl alcohol, isobutyl alcohol and the like.

The primary uses of sunscreens are to prevent sunburn and aid in the development of a tan. Secondarily, they serve to protect exposed areas of the body in susceptible individuals from the long-term hazards of skin cancer and premature aging. In addition, sunscreens can be used to protect against drug-related ultraviolet-induced photosensitivity.

For purposes of the present invention, the term "sunscreen agent" shall refer to the use of S(+)-ibuprofen as a sunscreen-sunburn preventive agent, a sunscreen-suntanning agent and/or a sunscreen-opaque sunblock agent. Each of those type of agents has been defined by the FDA advisory review panel as nonprescription topical analgesic, antirheumatic, otic, burn and sunburn prevention and treatment drug products as follows:

A sunscreen-sunburn preventive agent contains an active ingredient that absorbs 95% or more of the radiation in the ultraviolet range at wavelengths from 290-320 nm and thereby removes the sunburning rays;

A sunscreen-suntanning agent contains an active ingredient that absorbs at least 85% of the radiation in the ultra-violet range at wavelengths from 290-320 nm, but transmits ultraviolet wavelengths longer than 320 nm (such agents permit tanning in the average individual and also permits some erythema without pain);

A sunscreen-opaque sunblock agent has an opaque agent that reflects or scatters all radiation in the ultraviolet and visible range from 290-777 nm and thereby prevents or minimizes suntan and sunburn.

The following pharmaceutically acceptable topical ingredients are present in commercial sunscreens or sunblocks:

titanium dioxide, petrolatum, red petrolatum, benzophenone-3, isopropyl myristate, aloe vera extract, synthetic beeswax, cetyl palmitate, ceresin, lanolin, cetyl alcohol, alcohol, oleth-3 phosphate, synthetic spermaceti, glycerin, mineral oil, lanolin alcohol, cetyl stearyl glycol, lanolin oil, triethanolamine, carbomer 934, benzyl alcohol, menthol, camphor, essential oils, acrylic-acrylate copolymer, ammonium hydroxide, carbomer 934P, dimethicone, quaternium-15, stearic acid, stearyl alcohol, water, xanthan gum, SD alcohol 40, animal protein derivative, hydroxyethyl cellulose, choleth-24, hydroxypropyl cellulose, PPG-15 stearyl ether, propylene glycol dioctanoate, stearic acid, ozokerite, PEG-4 dilaurate, propylparaben, dihydroxyacetone, hydrocarbon oil, ointment base zinc oxide, opaque base, water-repellent cream base, caramel, perfume and flavors.

It would be advantageous for the topical composition of the present invention to have sufficient substantivity to withstand exposure of the skin to swimming, high humidity and sweating.

Generally, sunscreens should be applied approximately 30 minutes before exposure to the sun. However, there are exceptions, for instance, aminobenzoic acid and its esters are more effective if applied two hours before exposure. Pre-application of the topical S(+) ibuprofen composition prior to sun exposure to the skin is advantageous because it allows the S(+) ibuprofen to penetrate and perhaps bind with the skin.

The amount of S(+) ibuprofen useful in the topical preparations of the present invention is an amount sufficient to prevent or treat ultraviolet radiation-induced erythema.

Typical unit dosage forms for topical administration will contain about 0.5 wt. % to about 10 wt. %, preferably about 1 wt. % to about 35 wt. %, most preferably about 2.5 wt. % to about 3.5 wt. %, S(+) ibuprofen based on the entire weight of the composition per topical unit dose application. If the composition is intended for sustained release such as by using microcapsules or microspheres, much larger amounts of the active ingredient would of course be incorporated into an individual unit. As noted earlier, the composition and the method of the present invention is "substantially free of the R(−) ibuprofen."

The topical S(+) ibuprofen composition of the present invention may further be combined with other types of sun-protective and/or antierythema topical agents. Such agents may absorb 95 percent or more of the ultraviolet B radiation and thereby prevent or minimize the deleterious effects on human skin caused by excessive exposure to ultraviolet B (290 to 320 nm) and ultraviolet A (320 to 400 nm) radiation. Protection is afforded by the active chemical ingredients of a sunscreen through absorption, reflection and scattering of solar radiation impinging on the skin.

Topical sunscreens can fall within one of two categories: (1) chemical, and (2) physical sunscreens. Chemical sunscreens contain one or more UV-absorbing chemicals, and upon application of a thin and invisible film, act as filters and do not allow the penetration of ultraviolet radiation to the viable cells of the epidermis. Chemical sunscreens are usually colorless because they do not contain any visible light-absorbing chemicals and are, therefore, cosmetically acceptable to most persons provided they are a nonirritant to the skin and eyes, non-photosensitizing, stable, nonvolatile, and nonstaining to skin and clothes. Most of the commercial topical sunscreens contain one or more ultraviolet B absorbing chemicals in a moisturizing base. More recently, many leading brand-name sunscreens also contain ultraviolet A absorbing chemicals, especially the different benzophenones. The most widely used chemical sunscreens contain para-aminobenzoic acid (PABA), PABA esters (amyldimethyl PABA and octyldimethyl PABA), benzophenones (oxybenzone and sulisobenzone), cinnamates (octylmethoxy cinnamate and cinoxate), salicylates (homomenthyl salicylate), and anthranilates. To date, more than 21 such chemicals have been declared by the U.S. FDA as safe, effective agents in protecting skin against sunburn (see Table 1), and are listed under Category I (safe and approved).

TABLE 1

SUNSCREEN AGENTS

| Compound | Dose limits, % |
|---|---|
| p-aminobenzoic acid | 5.0–15.0 |
| glyceryl aminobenzoate | 3.0–5.0 |
| amyl p-dimethylamino benzoate (Padimate A) | 1.0–5.0 |
| 2-ethylhexyl-p-dimethylamino benzoate (Padimate O) | 1.4–8.0 |
| 2-ethoxy-ethylhexyl-p-methoxy cinnamate (cinnoxate) | 1.0–3.0 |
| diethanolamine-p-methoxycinnamate | 8.0–10.0 |
| ethylhexyl-p-methoxycinnamate | 2.0–7.5 |
| 2,2-dihydroxy-4-methoxybenzophenone (dioxybenzone) | 3.0 |
| 2-hydroxy-4-methoxybenzophenone (oxybenzone) | 2.0–6.0 |
| 2-hydroxy-4-methoxybenzophenone-5-sulfonic acid (sulisobenzone) | 5.0–10.0 |
| 2-ethyl-hexyl-2-cyano-3,3-diphenylacrylate | 7.0–10.0 |
| ethyl-4-bis-(hydroxypropyl)-amino benzoate | 1.0–5.0 |
| digalloyl trioleate | 1.0–5.0 |
| 2-ethylhexyl-salicylate | 3.0–5.0 |
| lawsone + dihydroxyacetone | 0.25–3.0 |
| 3,3,5-trimethylcyclohexyl salicylate (homosalate) | 4.0–15.0 |
| methylanthranilate | 3.5–4.0 |
| 2-phenyl-benzimidazole-5-sulfonic acid | 1.0–4.0 |
| triethanolamine salicylate | 5.0–12.0 |
| red veterinary petrolatum | 30.0–100 |
| titanium dioxide | 2.0–25.0 |

Several European sunscreen manufacturers often use p-methoxy-2-ethylhexylcinnamate, 2-phenylbenzimidazole-5-sulfonic acid, 2-phenyl-5-methoxybenzophenone, and 4-tert-butyl-4'-methoxydibenzoylmethane as ultraviolet A and B absorbing filters. The recommended concentration for each chemical may vary and is based on not only the solubility of the chemical in a given vehicle, but also the anticipated use of the sunscreen product as a total or partial block for the prevention of sunburn or acquisition of suntan responses. The formulation base (vehicle) used include alcohol plus glycerol or glycol, oil-in-water or water-in-oil lotion, cream, or ointment. The vehicle in which the ultraviolet radiation absorbing chemical is incorporated can determine whether a sunscreen remains effective under the general use condition involving prolonged sunbathing, sweating (sporting activities), and swimming. This adherent property to skin, known as "substantivity," varies considerably among commercially available sunscreen formulations, some of which are retained on the skin and others of which are washed off easily after sweating or swimming.

Table 2 identifies several commercial chemical sunscreen preparations along with their ingredients and type of composition.

TABLE 2

| Trade name | Ingredients | Type of sunscreen |
|---|---|---|
| PABA sunscreens: | | |
| PreSun-15 | | Clear lotion |
| Pabanol | 5% PABA in 50%–70% ethyl alcohol | Clear lotion |
| Sunbrella | | Clear lotion |
| PreSun-15 | | Gel |
| PABA ester sunscreens: | | |
| Block out | 3.3% isoamyl-p-N,N-dimethyl amino-benzoate (padimate-A) | Lotion/gel |
| PABAFILM | 3.3% isoamyl-p-N,N-dimethyl amino-benzoate (padimate-A) | Lotion/gel |
| Sundown | 3.3% isoamyl-p-N,N-dimethyl amino-benzoate (padimate-A) | Lotion |
| Original Eclipse | 3.5% padimate-A + 3.0% octyldimethyl PABA | Lotion |
| Aztec | 5.0% homomenthyl salicylate + 2.5% amyl-p-dimethyl aminobenzoate | Lotion |
| Sea & Ski | 3.3% octyldimethyl PABA | Cream |
| Marbert Sun Creme | benzyliden-camphor phenylbenzimidazole-5-sulfonic acid + isopropyl dibenzoyl methane | Cream |
| PABA-ester combination sunscreens: | | |
| Coppertone Super Shade-15 | 7% octyldimethyl PABA + 3% oxybenzone | Milky lotion |
| Total Eclipse-15 | 2.5% glyceryl PABA + 2.5% octyldimethyl PABA + 2.5% oxybenzone | Milky lotion |
| MMM-What-A-Tan! | 3.0% octyldimethyl PABA + 2.5% benzophenone-3 | Milky lotion |
| PreSun-15 (water-resistant) | 8% padimate-O + 3% oxybenzone | Milky lotion |
| Clinique-19 | phenyl-benzimidazole-5-sulfonic acid + 2.5% octyldimethyl PABA | Milky lotion |
| Sundown-15 (sunblock) | 7% padimate-O + 5% octylsalicylate + 4% oxybenzone | Milky lotion |
| Bain de Soleil | 7.0% padimate-O + 2.5% oxybenzone + 0.5% dioxybenzone | White cream |
| Elizabeth Arden Suncare Creme-15 | padimate-O + oxybenzone | White cream |
| Estee Lauder-15 | phenyl-benzimidazole-5-sulfonic acid + dimethyl PABA | White cream |
| Rubenstein Gold Beauty-15 | ethyl-hexyl-p-methoxycinnamate + octyldimethyl PABA | Yellow gel |
| Block Out-15 | 7% octyldimethyl PABA + 3% oxybenzone | Creamy lotion |
| Shiseido-15 | 6.5% titanium dioxide + 2.5% octyldimethyl PABA + 0.3% benzophenone-3 | Lotion |
| Non-PABA sunscreens: | | |
| Piz Buin-8 | 5% ethyl-hexyl-p-methoxycinnamate + 3% 2-hydroxy-4-methoxybenzophenone + 4% 2-phenyl-benzimidazole sulfonic acid | Cream |
| Piz Buin-8 | 5% ethyl-hexyl-p- | Milky lotion |

TABLE 2-continued

| Trade name | Ingredients | Type of sunscreen |
|---|---|---|
| TIScreen-15 | methoxycinnamate + 3% 2-hydroxy-4-methoxybenzophenone | |
| Piz Buin-4 | 4.5% ethyl-hexyl-p-methoxycinnamate | Milky lotion |
| UVAL | 10% 2-hydroxy-4-methoxybenzophenone-5-sulfonic acid | Milky lotion |
| Coppertone | 8% homomenthyl-salicylate | Lotion |
| Ultra Vera-20 (Cheesebrough-Ponds) | octylmethoxycinnamate + 2-hydroxy-4-methoxybenzophenone | Milky lotion |
| Piz Buin Gletscher Creme-15 | cinnamide + dibenzoyl-methane | Yellow lotion |
| Piz Buin-12 | 4.5% octyl-methoxy-cinnamate + 4.5% zinc oxide + 4.5% talc + 2.2% benzophenone-3 | Milky lotion |

Physical sunscreens are usually opaque formulations and contain ingredients particulate in nature than do not selectively absorb ultraviolet radiation, but, when applied as a thin film, primarily reflect and scatter ultraviolet and visible radiation because of the size of the particles and the thickness of the film. These include titanium dioxide (5% to 20%), talc (magnesium silicate), magnesium oxide, zinc oxide, kaolin, ferric chloride, and ichthyol (ichthammol). Zinc oxide appears to be the most effective. These formulations are cosmetically unpleasing, unacceptable to many patients, and are often occlusive and messy to use. Physical sunscreens are, however, essential for those patients who are unusually sensitive to ultraviolet radiation as well as visible radiation; these are usually applied to limited areas such as the nose, lips, or helix of the ear.

Table 3 identifies several commercial physical sunscreen preparations along with their ingredients and type of composition.

TABLE 3

| Physical sunscreens | | |
|---|---|---|
| Tradename | Ingredients | Type of Sunscreen |
| A-Fil | | Cream |
| RV Paque | titanium dioxide + | Cream |
| Shadow | oxide + talc, | Cream |
| Reflecta | kaolin, iron oxide, | Cream |
| Covermark | or red veterinary | Cream |
| Clinique | petrolatum | Cream |

S(+) ibuprofen may be combined along with any of the compounds identified in any of the Tables identified above as a topical vehicle for administration.

For cosmetic rather than therapeutic needs, the patient may desire a suntan product. In many cases, suntan products differ from sunscreens only by having a lower concentration of the sunscreen agent. The concentration of the active ingredient is an important factor in judging the use and effectiveness of a product. For example, SunDare Lotion, a suntan product, contains 1.75% cinoxate, while Maxafil Cream, a sunscreen product, contains 4% (about twice as much as the suntan product) and 5% menthyl anthranilate, a second sunscreen.

Further, the sunburn/sunscreen product of the present invention may include a burn or sunburn treatment component such as an anesthetic, antimicrobial or another ingredient.

The anesthetic component of commerical products presently include:

benzocaine, lidocaine hydrochloride, butamben picrate, dibucaine, tetracaine hydrochloride, tripelennamine, and menthol benzocaine.

The antimicrobial component of commercial products currently include:

benzethonium chloride, benzalkonium chloride, povidone-iodine, chloroxylenol, chlorobutanol, 8-hydroxyquinoline, phenol, 8-hydroxyquinoline sulfate, cresol-camphor complex, chlorothymol, methlbenzethonium chloride, triclosan, benzyl alcohol, and parahydracin.

The S(+) ibuprofen for use in the method and compositions of the present invention can be prepared by a variety of methods, such as by resolution of racemic ibuprofen.

Resolution of racemic ibuprofen has been described in the literature. Kaiser et al, *J. Pharm. Sci.*, Vol. 65, No. 2, 269-273 (February 1976) added S(−) α-methylbenzylamine dropwise, with stirring, to a cooled solution of racemic ibuprofen in ether. The solid S(−) α-methylbenzylamine salt of S(+) ibuprofen thus obtained was removed by filtration, recrystallized first from isopropanol and then from methanol, acidified with 3N aqueous sulfuric acid, extracted with ether and washed with water and saline solution. The ether extract was evaporated to dryness and the resultant white solid was recrystallized from ethanol to give S(+) ibuprofen, m.p. 50°-52°, $[\alpha]_D + 57°$, with 95% optical purity as determined by GLC analysis as the S(−) α-methylbenzylamide derivative. Cox et al, *J. Pharmocol. Exp. Ther.*, Vol. 232, No. 3, 636-643 (March 1985), using Kaiser et al's method, were able to obtain an S(+) ibuprofen preparation which was 99% S isomer and 1% R isomer (w/w).

Generally speaking, the S(+) isomer can be separated from racemic ibuprofen by preparing a salt of ibuprofen with an alkaloid or similar resolving agent such as cinchonidine, then separating the products by fractional crystallization from a solvent in which the dextrorotatory isomer is least soluble. The d-salt can then be acid cleaved to yield S(+) ibuprofen. Compare, for example, Alvarez U.S. Pat. No. 3,637,767, issued Jan. 25, 1972, which relates to resolution of naproxen and related compounds.

When S(+) ibuprofen is to be employed in the form of a pharmaceutically acceptable salt thereof, such salt may be conveniently prepared by direct salification of S(+) ibuprofen. Compare Armitage et al U.S. Pat. No. 4,501,727, issued Feb. 26, 1985, which describes the N-methyl-D-glucamine salt of flurbiprofen. Such a salt, if sufficiently soluble in water, may be useful in the preparation of aqueous solutions of S(+) ibuprofen.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalents of the following claims.

What is claimed is:

1. A method for preventing or treating ultraviolet radiation-induced erythema in a human mammal exposed to ultraviolet radiation or suffering from ultraviolet radiation-induced erythema and in need of such prevention or treatment, comprising topically administering to such mammal a composition comprising a unit dosage amount effective to prevent or treat ultraviolet radiation-induced erythema of the S(+) ibuprofen enantiomer, and said enantiomer being substantially free of its R(−) ibuprofen antipode.

2. The method according to claim 1, wherein the weight ratio of S(+) ibuprofen to R(−) ibuprofen is greater than 9:1.

3. The method according to claim 2, wherein the weight ratio of S(+) ibuprofen to R(−) ibuprofen is greater than 20:1.

4. The method according to claim 3, wherein the weight ratio of S(+) ibuprofen to R(−) ibuprofen is greater than 97:3.

5. The method according to claim 4, wherein the weight ratio of S(+) ibuprofen to R(−) ibuprofen is approximately equal to or greater than 99:1.

6. The method according to claim 1, comprising topically administering to such mammal from about 0.5 wt. % to about 10 wt. % S(+) ibuprofen, based on the weight of the entire composition.

7. The method according to claim 1, comprising topically administering to such mammal from about 1.0 wt. % to about 5.0 wt. % S(+) ibuprofen, based on the weight of the entire composition.

8. The method according to claim 1, comprising topically administering to such mammal from about 2.5 wt. % to about 3.5 wt. % S(+) ibuprofen, based on the weight of the entire composition.

9. The method according to claim 2, comprising topically administering to such mammal from about 0.5 wt. % to about 10 wt. % S(+) ibuprofen, based on the weight of the entire composition.

10. The method according to claim 2, comprising topically administering to such mammal from about 1.0 wt. % to about 5.0 wt. % S(+) ibuprofen, based on the weight of the entire composition.

11. The method according to claim 2, comprising topically administering to such mammal from about 2.5 wt. % to about 3.5 wt. % S(+) ibuprofen, based on the weight of the entire composition.

12. The method according to claim 3, comprising topically administering to such mammal from about 0.5 wt. % to about 10 wt. % S(+) ibuprofen, based on the weight of the entire composition.

13. The method according to claim 3, comprising topically administering to such mammal from about 1.0 wt. % to about 5.0 wt. % S(+) ibuprofen, based on the weight of the entire composition.

14. The method according to claim 3, comprising topically administering to such mammal from about 2.5 wt. % to about 3.5 wt. % S(+) ibuprofen, based on the weight of the entire composition.

15. The method according to claim 4, comprising topically administering to such mammal from about 0.5 wt. % to about 10 wt. % S(+) ibuprofen, based on the weight of the entire composition.

16. The method according to claim 4, comprising topically administering to such mammal from about 1.0 wt. % to about 5.0 wt. % S(+) ibuprofen, based on the weight of the entire composition.

17. The method according to claim 4, comprising topically administering to such mammal from about 2.5 wt. % to about 3.5 wt. % S(+) ibuprofen, based on the weight of the entire composition.

18. The method according to claim 5, comprising topically administering to such mammal from about 0.5 wt. % to about 10 wt. % S(+) ibuprofen, based on the weight of the entire composition.

19. The method according to claim 5, comprising topically administering to such mammal from about 1.0 wt. % to about 5.0 wt. % S(+) ibuprofen, based on the weight of the entire composition.

20. The method according to claim 5, comprising topically administering to such mammal from about 2.5 wt. % to about 3.5 wt. % S(+) ibuprofen, based on the weight of the entire composition.

21. The method according to claim 1, wherein the S(+) enantiomer is topically administered as a lotion.

22. The method according to claim 1, wherein the S(+) enantiomer is topically administered as a gel.

23. The method according to claim 1, wherein the S(+) enantiomer is topically administered as a solution.

24. The method according to claim 1, wherein said composition further comprises a unit dosage amount effective to prevent or treat ultraviolet radiation-induced erythema of an additional sunscreen.

25. The method according to claim 24, wherein said additional sunscreen is selected from the group consisting of p-aminobenzoic acid, amyldimethyl p-aminobenzoic acid, octyldimethyl p-aminobenzoic acid, octylmethoxy cinnamate, homomenthyl salicylate, glyceryl aminobenzoate, amyl p-dimethylamino benzoate 2-ethylhexyl-p-dimethylamino benzoate, 2-ethoxyethylhexyl-p-methoxy cinnamate, diethanolamine-p-methoxycinnamate, ethylhexyl-p-methoxycinnamate, 2,2-dihydroxy-4-methoxybenzophenone, 2-hydroxy-4-methoxybenzophenone, 2-hydroxy-4-methoxybenzophenone-5-sulfonic acid, 2-ethyl-hexyl-2-cyano-3,3-diphenylacrylate, ethyl-4-bis-(hydroxypropyl)-amino benzoate, digalloyl trioleate, 2-ethylhexyl-salicylate, lawsone +dihydroxyacetone, 3,3,5-trimethylcyclohexyl salicylate, methylanthranilate, 2-phenyl-benzimidazole-5-sulfonic acid, triethanolamine salicylate, red veterinary petrolatum and titanium dioxide.

26. The method according to claim 25, wherein said additional sunscreen is selected from the group consisting of para-aminobenzoic acid, amyldimethyl para-aminobenzoic acid, octyldimethyl para-aminobenzoic acid, 2-hydroxy-4-methoxybenzophenone and 2-hydroxy-4-methoxybenzophenone-5-sulfonic acid.

27. The method according to claim 26, wherein said additional sunscreen is para-aminobenzoic acid.

28. A pharmaceutical composition of matter adapted for topical administration for preventing or treating ultraviolet radiation-induced erythema in a human mammal exposed to ultraviolet radiation or suffering from ultraviolet radiation-induced erythema, said composition comprising a unit dosage topically effective amount to prevent or treat ultraviolet radiation-induced erythema of the S(+) ibuprofen enantiomer, said enantiomer being substantially free of its R(−) ibuprofen antipode, and a nontoxic topical pharmaceutically acceptable carrier or diluent therefor.

29. The composition according to claim 28, wherein the weight ratio of S(+) ibuprofen to R(−) ibuprofen is greater than 9:1.

30. The composition according to claim 29, wherein the weight ratio of S(+) ibuprofen to R(−) ibuprofen is greater than 20:1.

31. The composition according to claim 30, wherein the weight ratio of S(+) ibuprofen to R(−) ibuprofen is greater than 97:3.

32. The composition according to claim 31, wherein the weight ratio of S(+) ibuprofen to R(−) ibuprofen is approximately equal to or greater than 99:1.

33. The composition according to claim 28, comprising about 0.5 wt. % to about 10 wt. % S(+) ibuprofen, based on the weight of the entire composition.

34. The composition according to claim 28, comprising about 1.0 wt. % to about 5.0 wt. % S(+) ibuprofen, based on the weight of the entire composition.

35. The composition according to claim 28, comprising about 2.5 wt. % to about 3.5 wt. % S(+) ibuprofen, based on the weight of the entire composition.

36. The composition according to claim 29, comprising about 0.5 wt. % to about 10 wt. % S(+) ibuprofen, based on the weight of the entire composition.

37. The composition according to claim 29, comprising about 1.0 wt. % to about 5.0 wt. % S(+) ibuprofen, based on the weight of the entire composition.

38. The composition according to claim 29, comprising about 2.5 wt. % to about 3.5 wt. % S(+) ibuprofen, based on the weight of the entire composition.

39. The composition according to claim 30, comprising about 0.5 wt. % to about 10 wt. % S(+) ibuprofen, based on the weight of the entire composition.

40. The composition according to claim 30, comprising about 1.0 wt. % to about 5.0 wt. % S(+) ibuprofen, based on the weight of the entire composition.

41. The composition according to claim 30, comprising about 2.5 wt. % to about 3.5 wt. % S(+) ibuprofen, based on the weight of the entire composition.

42. The composition according to claim 31, comprising about 0.5 wt. % to about 10 wt. % S(+) ibuprofen, based on the weight of the entire composition.

43. The composition according to claim 31, comprising about 1.0 wt. % to about 5.0 wt. % S(+) ibuprofen, based on the weight of the entire composition.

44. The composition according to claim 31, comprising about 2.5 wt. % to about 3.5 wt. % S(+) ibuprofen, based on the weight of the entire composition.

45. The composition according to claim 32, comprising about 0.5 wt. % to about 10 wt. % S(+) ibuprofen, based on the weight of the entire composition.

46. The composition according to claim 32, comprising about 1.0 wt. % to about 5.0 wt. % S(+) ibuprofen, based on the weight of the entire composition.

47. The composition according to claim 32, comprising about 2.5 wt. % to about 3.5 wt. % S(+) ibuprofen, based on the weight of the entire composition.

48. The composition according to claim 28, wherein the S(+) enantiomer is topically administered as a lotion.

49. The composition according to claim 28, wherein the S(+) enantiomer is topically administered as a gel.

50. The composition according to claim 28, wherein the S(+) enantiomer is topically administered as a solution.

51. The composition according to claim 28, wherein said composition further comprises a unit dosage amount effective to prevent or treat ultraviolet radiation-induced erythema of an additional sunscreen.

52. The composition according to claim 51, wherein said additional sunscreen is selected from the group consisting of p-aminobenzoic acid, amyldimethyl p-aminobenzoic acid, octyldimethyl p-aminobenzoic acid, octylmethoxy cinnamate, homomenthyl salicylate, glyceryl aminobenzoate, amyl p-dimethylamino benzoate 2-ethylhexyl-p-dimethylamino benzoate, 2-ethoxyethylhexyl-p-methoxy cinnamate, diethanolamine-p-methoxycinnamate, ethylhexyl-p-methoxycinnamate, 2,2-dihydroxy-4-methoxybenzophenone, 2-hydroxy-4-methoxybenzophenone, 2-hydroxy-4-methoxybenzophenone-5-sulfonic acid, 2-ethyl-hexyl-2-cyano-3,3-diphenylacrylate, ethyl-4-bis-(hydroxypropyl)-amino benzoate, digalloyl trioleate, 2-ethylhexyl-salicylate, lawsone +dihydroxyacetone, 3,3,5-trimethylcyclohexyl salicylate, methylanthranilate, 2-phenyl-benzimidazole-5-sulfonic acid, triethanolamine salicylate, red veterinary petrolatum and titanium dioxide.

53. The composition according to claim 52, wherein said additional sunscreen is selected from the group consisting of para-aminobenzoic acid, amyldimethyl para-aminobenzoic acid, octyldimethyl para-aminobenzoic acid, 2-hydroxy-4-methoxybenzophenone and 2-hydroxy-4-methoxybenzophenone-5-sulfonic acid.

54. The composition according to claim 53, wherein said additional sunscreen is para-aminobenzoic acid.

* * * * *